(12) United States Patent
Brady et al.

(10) Patent No.: US 9,649,039 B1
(45) Date of Patent: May 16, 2017

(54) MOBILE PLETHYSMOGRAPHIC DEVICE

(71) Applicant: Impact Sports Technologies, Inc., Las Vegas, NV (US)

(72) Inventors: Donald Brady, Las Vegas, NV (US); Nikolai Rulkov, San Diego, CA (US); Mark Hunt, San Diego, CA (US)

(73) Assignee: Impact Sports Technologies, Inc., Las Vegas, NV (US)

( * ) Notice: Subject to any disclaimer, the term of this patent is extended or adjusted under 35 U.S.C. 154(b) by 0 days.

(21) Appl. No.: 14/809,200

(22) Filed: Jul. 25, 2015

Related U.S. Application Data

(63) Continuation-in-part of application No. 14/641,315, filed on Mar. 7, 2015, now Pat. No. 9,144,385, which is a continuation of application No. 14/485,770, filed on Sep. 14, 2014, now Pat. No. 8,974,396.

(60) Provisional application No. 62/028,811, filed on Jul. 25, 2014.

(51) Int. Cl.
*A61B 5/02* (2006.01)
*A61B 5/024* (2006.01)
*A61B 5/00* (2006.01)

(52) U.S. Cl.
CPC ...... *A61B 5/02416* (2013.01); *A61B 5/02028* (2013.01); *A61B 5/02427* (2013.01); *A61B 5/681* (2013.01); *A61B 5/7221* (2013.01); *A61B 5/7282* (2013.01)

(58) Field of Classification Search
CPC ............ A61B 5/02416; A61B 5/02028; A61B 5/02427
See application file for complete search history.

(56) References Cited

U.S. PATENT DOCUMENTS

| | | | |
|---|---|---|---|
| 6,551,252 B2 * | 4/2003 | Sackner | A61B 5/0205 600/301 |
| 2013/0138002 A1 * | 5/2013 | Weng | A61B 5/0205 600/508 |

* cited by examiner

*Primary Examiner* — Robert N Wieland
(74) *Attorney, Agent, or Firm* — Clause Eight IPS; Michael Catania

(57) ABSTRACT

A mobile plethysmographic device for detecting a Peripheral Artery Disease ("PAD") event or other arrhythmia event is disclosed herein. The mobile plethysmographic device generates a pleth waveform, which is automatically screened by algorithms that measure the waveform to correlate, detect and store aberrations related to heart anomalies. A peripheral artery disease event for a patient is determined based on a quantative measure of blood flow in the extremities based on the differential in amplitude in the pleth signal between the arm and the two lower extremities. The changes in amplitude from the arm and one or both lower extremities can indicate PAD.

6 Claims, 17 Drawing Sheets

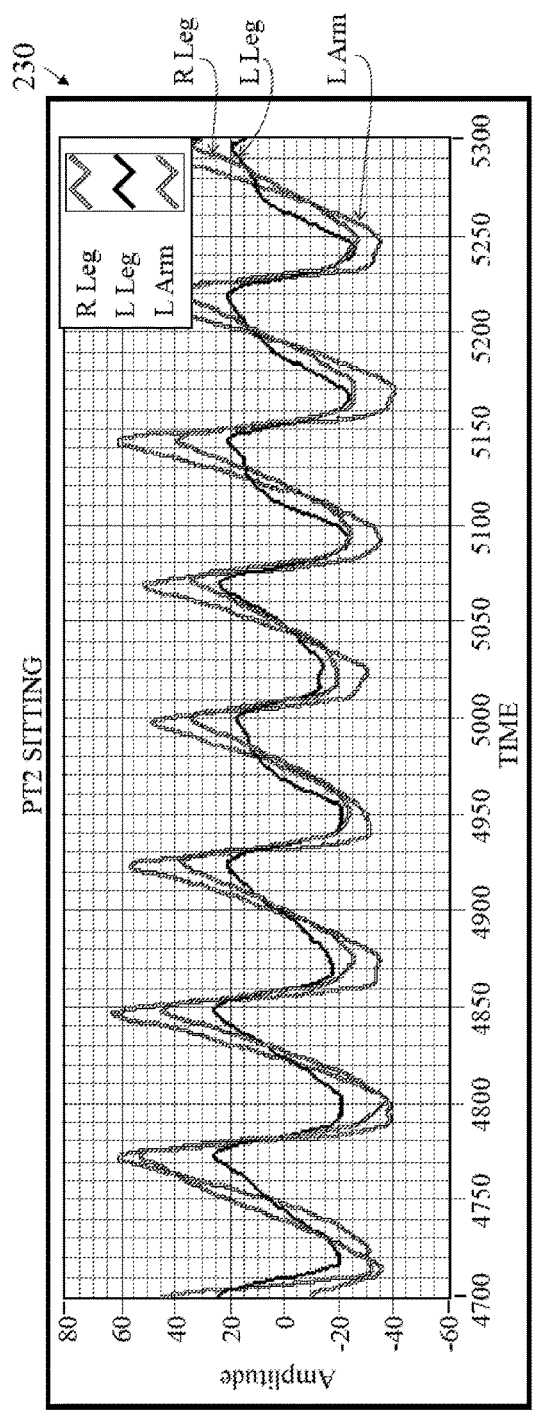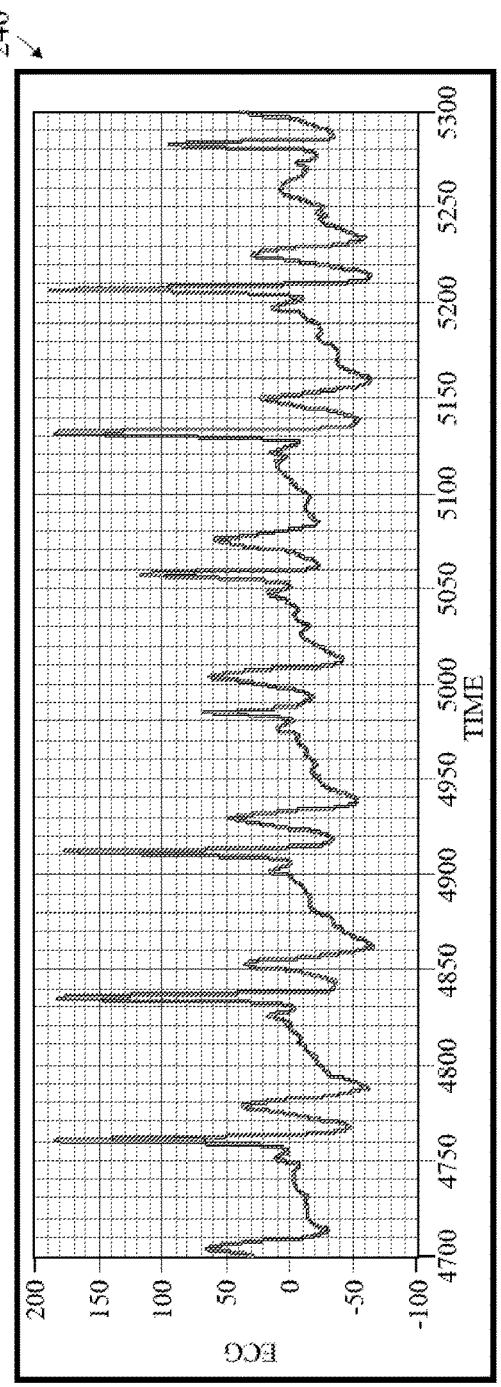
FIG. 18
FIG. 18A

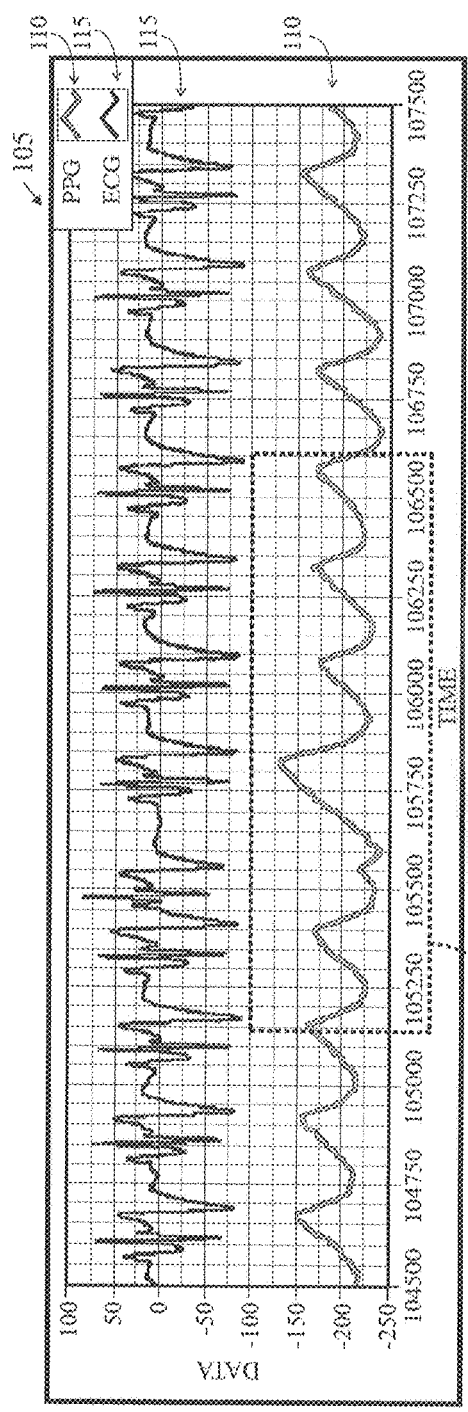
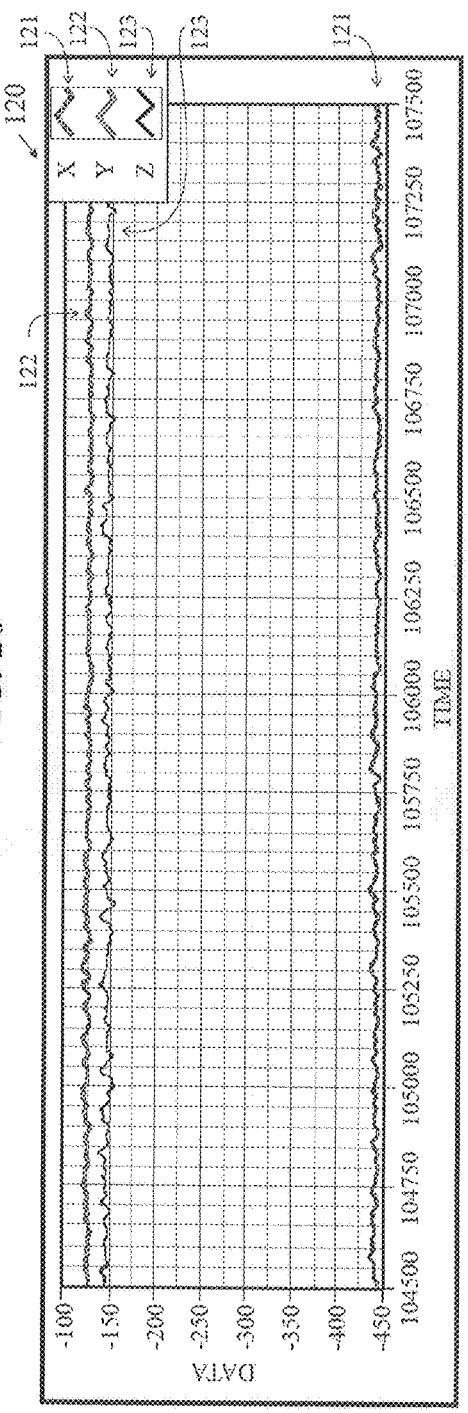
FIG. 20
FIG. 20A

MOBILE PLETHYSMOGRAPHIC DEVICE

CROSS REFERENCES TO RELATED APPLICATIONS

The present application claims priority to U.S. Provisional Patent Application No. 62/028,811, filed on Jul. 25, 2014, and is a continuation-in-part application of U.S. patent application Ser. No. 14/641,315, filed on Mar. 7, 2015, now U.S. Pat. No. 9,144,385, issued on Sep. 29, 2015, which is a continuation of U.S. patent application Ser. No. 14/485,770, filed on Sep. 14, 2014, now U.S. Pat. No. 8,974,396, issued on Mar. 10, 2015, all of which are hereby incorporated by reference in their entireties.

STATEMENT REGARDING FEDERALLY SPONSORED RESEARCH OR DEVELOPMENT

Not Applicable

BACKGROUND OF THE INVENTION

Field of the Invention

The present invention is related to plethysmographic devices. More specifically, the present invention relates to a method for determining a premature atrial contraction event using a mobile plethysmographic device.

Description of the Related Art

There is no easy method to determine if someone is suffering from a peripheral artery disease.

Peripheral artery disease is often associated with high blood pressure, diabetes, heart disease, stroke, sedentary lifestyle and aging—cholesterol and fat plaque blocks circulation to vital arteries, often in the legs and feet. Diagnosis for Peripheral Artery Disease ("PAD") is typically done by comparing results from two blood pressure cuffs. To help determine how well a patient's blood is flowing, experienced clinicians use the ankle-brachial index, a painless, inexpensive exam, to compare blood pressure in a patient's feet to the blood pressure in his arms. Particularly lower-leg pain, is misdiagnosed and primary care doctors make referrals to orthopedic surgeons, nerve specialists and podiatrists.

Arrhythmias are caused by problems with the heart's electrical system. An arrhythmia is a heartbeat that's too fast, too slow or irregular (uneven). The electrical signals may fire too fast (tachycardia) or too slowly (bradycardia), or in an uneven (irregular) way. When you have an arrhythmia, your heart may seem to skip beats or flutter. Fibrillation is an abnormal firing of signals within an area of the heart causing a disorganized beat. Abnormal electrical signals can originate in different areas of the heart (such as the atria or ventricles) causing arrhythmias.

Tachycardia is a heart rate that exceeds the normal range. In general, a resting heart rate over 100 beats per minute is accepted as tachycardia. Tachycardia can be caused by various factors that often are benign. However, tachycardia can be dangerous, depending on the speed and type of rhythm.

Bradycardia is the resting heart rate of under 60 beats per minute ("BPM"), although it is seldom symptomatic until the rate drops below 50 BPM. It sometimes results in fatigue, weakness, dizziness, and at very low rates fainting. A waking heart rate below 40 BPM is considered absolute bradycardia.

Sinus arrhythmia involves cyclic changes in the heart rate during breathing. It is very common in children and often found in young adults. Patients with sinus arrhythmia do not experience any cardiovascular symptoms. The sinus node rate can change with inspiration/expiration, especially in younger people. The heart rate speeds up with inspiration (since it inhibits your vagal nerve) and decreases with expiration (stimulates your vagal nerve). Sick sinus syndrome (SSS) occurs when over time the sinus node scars and becomes replaced with fibrous tissues. SSS contains a spectrum of arrhythmias including severe sinus bradycardia, tachycardic-bradycardic syndrome (tachy-brady syndrome), or sinus exit block/sinus pauses. Also known as "tachy-brady syndrome," sick sinus syndrome is a common condition that affects the elderly, accounting for the majority of patients undergoing pacemaker implantation in the U.S.

Premature Atrial Contractions (PACs) are amongst the most common forms of arrhythmias. It is due to the premature discharge of an electrical impulse in the atrium, causing a premature contraction. A PAC is premature, because it occurs earlier than the next regular beat should have occurred.

Premature ventricular contractions (PVCs) are premature heartbeats originating from the ventricles of the heart. Premature ventricular contractions are premature because they occur before the regular heartbeat.

In atrial fibrillation, the normal regular electrical impulses generated by the sinoatrial node in the right atrium of the heart are overwhelmed by disorganized electrical impulses usually originating in the roots of the pulmonary veins. This leads to irregular conduction of ventricular impulses that generate the heartbeat. AF may occur in episodes lasting from minutes to days (paroxysmal AF) or may be permanent in nature. Many medical conditions increase the risk of AF, in particular mitral stenosis (narrowing of the mitral valve of the heart).

There is presently no simple, consistent and reliable way to diagnose and quantify PAD and its progression in patients at any stage. This is particularly true for primary care physicians who are the first providers to typically diagnose PAD. Early detection can support early preventative measures to mitigate development of the disease with attendant damage to the patient and cost. Currently, use of ultrasound to determine if there is a blockage of an artery or use of a blood pressure monitor on the leg and one on the arm simultaneously to try to ascertain a restricted blood flow are the most common means of diagnosing PAD. Doctors essentially rely on their experience and analysis.

The prior art requires ECG devices attached to a patient in order to determine if a PAC event is occurring. Due to all of this effort required to determine if a PAC event using the ECG device, most patients fail to get diagnosed. Thus, there is a need for a mobile plethysmographic device that can be worn for an extended period and provide PAC information to a user.

BRIEF SUMMARY OF THE INVENTION

The present invention is a mobile plethysmographic device worn on the arm or wrist that continuously monitors heart rate on a beat to beat basis to screen for anomalies such as but not limited to Premature Ventricular Contractions ("PVC"), Premature Arial Contractions ("PAC"), PAD, and Heart Arrhythmias, Tachycardia or Bradycardia. The mobile plethysmographic device generates a photoplethysmograph ("PPG") signal, also referred to as a pleth waveform, which is analyzed for anomalies. The mobile plethysmographic device uses an integrated accelerometer to validate the accuracy of the pleth waveform by detecting motion that is disturbing and corrupting the pleth waveform or to indicate a stable measurement with no motion to validate the waveform data with a high degree of confidence. The pleth waveforms are directly correlated to various heart anomalies and used as a simple, accurate, and convenient means of screening patients for heart conditions. The pleth waveform data is automatically screened by algorithms that measure the waveform to correlate, detect and store aberrations related to heart anomalies. The mobile plethysmographic also permits the wearer to send a manual command to the mobile plethysmographic device to store data if the wearer senses an event is occurring. The mobile plethysmographic device is preferably worn continuously, including during sleep to monitor, screen and store heart rate data. The mobile plethysmographic device is also used to screen for heart conditions related to sleep apnea.

The mobile plethysmographic device has the capability to store onboard heart rate data and the capability to download data for further review via Bluetooth, Bluetooth Low Energy, ANT, 802.11 protocols or other similar wireless data transfer means. The mobile plethysmographic device also has the means to transfer data via a USB using a wired interface from the mobile plethysmographic device to any USB host capable device.

The device, which measures blood volume, is an alternative to the current methods and provides a quantitative measure of blood flow in the extremities based on the differential in amplitude in the pleth signal between the arm and the two lower extremities. The changes in amplitude from the arm and one or both lower extremities can indicate PAD. When measurements are taken over time they can also be used to diagnose the progression of the disease and support effective treatment.

The device uses an integrated accelerometer to validate the accuracy of the waveform by detecting motion that is disturbing and corrupting the pleth waveform or to indicate a stable measurement with no motion to validate the waveform data with a high degree of confidence. The pleth waveforms can be directly correlated to various heart anomalies and be used as a simple, accurate, and convenient means of screening patients for heart conditions. The pleth waveform data can be automatically screened by creating algorithms that measure the waveform to correlate, detect and store aberrations related to heart anomalies. The device will also permit the wearer to send a manual command to the device to store data if they sense an event is taking place. The device can be worn continuously, including during sleep to monitor, screen and store heart rate data. Device may be used to screen for heart conditions related to PAD.

One aspect of the present invention is a method for determining a premature atrial contraction (PAC) event for a patient. The method comprises generating a plethysmographic waveform for a patient from a digitized electrical signal generated by an optical sensor controlled by a processor that acquires the waveform data and processes it. The optical sensor, the analog front-end (AFE) for sensor signal conditioning and the processor are on a mobile device. The plethysmographic signal comprises a plurality of pulse waves. The method steps are done at the processor on the mobile device Another aspect is a method for determining a PAD event for a patient. The method begins by generating a first plethysmographic signal for an arm position for a patient from an optical signal generated by an optical sensor, and digitized, processed and synchronized by a processor, the optical sensor and processor on a first mobile plethysmographic device, the first plethysmographic mobile device comprising a wireless transceiver for transmitting and receiving wireless communications using a first communication protocol, the first plethysmographic signal comprising a first plurality of pulse waves. Then, generating a second plethysmographic signal for a right leg position for a patient from an optical signal generated by an optical sensor, and digitized, processed and synchronized by a processor, the optical sensor and processor on a second mobile plethysmographic device, the second plethysmographic mobile device comprising a wireless transceiver for transmitting and receiving wireless communications using the first communication protocol, the second plethysmographic signal comprising a second plurality of pulse waves. Further, generating a third plethysmographic signal for a left leg position for a patient from an optical signal generated by an optical sensor and digitized, processed and synchronized by a processor, the optical sensor and processor on a third mobile plethysmographic device, the third mobile plethysmographic device comprising a wireless transceiver for transmitting and receiving wireless communications using the first communication protocol, the third plethysmographic signal comprising a third plurality of pulse waves. Next, transmitting synchronized data for the second plethysmographic signal and synchronized data for the third plethysmographic signal to the wireless transceiver of the first mobile plethysmographic device. Then, transmitting synchronized data for the first plethysmographic signal, synchronized data for the second plethysmographic signal and synchronized data for the third plethysmographic signal from the wireless transceiver of the first mobile device to a wireless transceiver of a processing device, wherein the first plethysmographic signal, the second plethysmographic signal and the third plethysmographic signal are time synchronized for comparison on a time basis. Further, measuring a plurality of amplitudes of each of the first plurality of pulse waves, the second plurality of pulse waves, and the third plurality of pulse waves. Also, measuring a plurality of delays of each of the first plurality of pulse waves, the second plurality of pulse waves, and the third plurality of pulse waves. Then, comparing the plurality of amplitudes of each of the first plurality of pulse waves, the second plurality of pulse waves, and the third plurality of pulse waves. Then, comparing the plurality of delays of each of the first plurality of pulse waves, the second plurality of pulse waves, and the third plurality of pulse waves. And lastly, determining at the processor a PAD event for the patient based on a difference between the plurality of amplitudes of each of the first plurality of pulse waves, the second plurality of pulse waves, and the third plurality of pulse waves, and a difference between the plurality of delays of each of the first plurality of pulse waves, the second plurality of pulse waves, and the third plurality of pulse waves.

The processing device is preferably a smart phone or smart device.

Alternatively, the processing device is a desktop computer.

Having briefly described the present invention, the above and further objects, features and advantages thereof will be recognized by those skilled in the pertinent art from the following detailed description of the invention when taken in conjunction with the accompanying drawings.

BRIEF DESCRIPTION OF THE SEVERAL VIEWS OF THE DRAWINGS

FIG. 18 is a graph of time versus amplitude for a $2^{nd}$ patient sitting up.

FIG. 18A is a graph of time versus amplitude for an ECG.

FIG. 20 is a graph of time versus amplitude for a PPG and ECG.

FIG. 20A is a graph of motion over the same time period as the graph of FIG. 20, with the motion detected by an X, Y, and Z accelerometer on the mobile plethysmographic device.

DETAILED DESCRIPTION OF THE INVENTION

Figure 1:
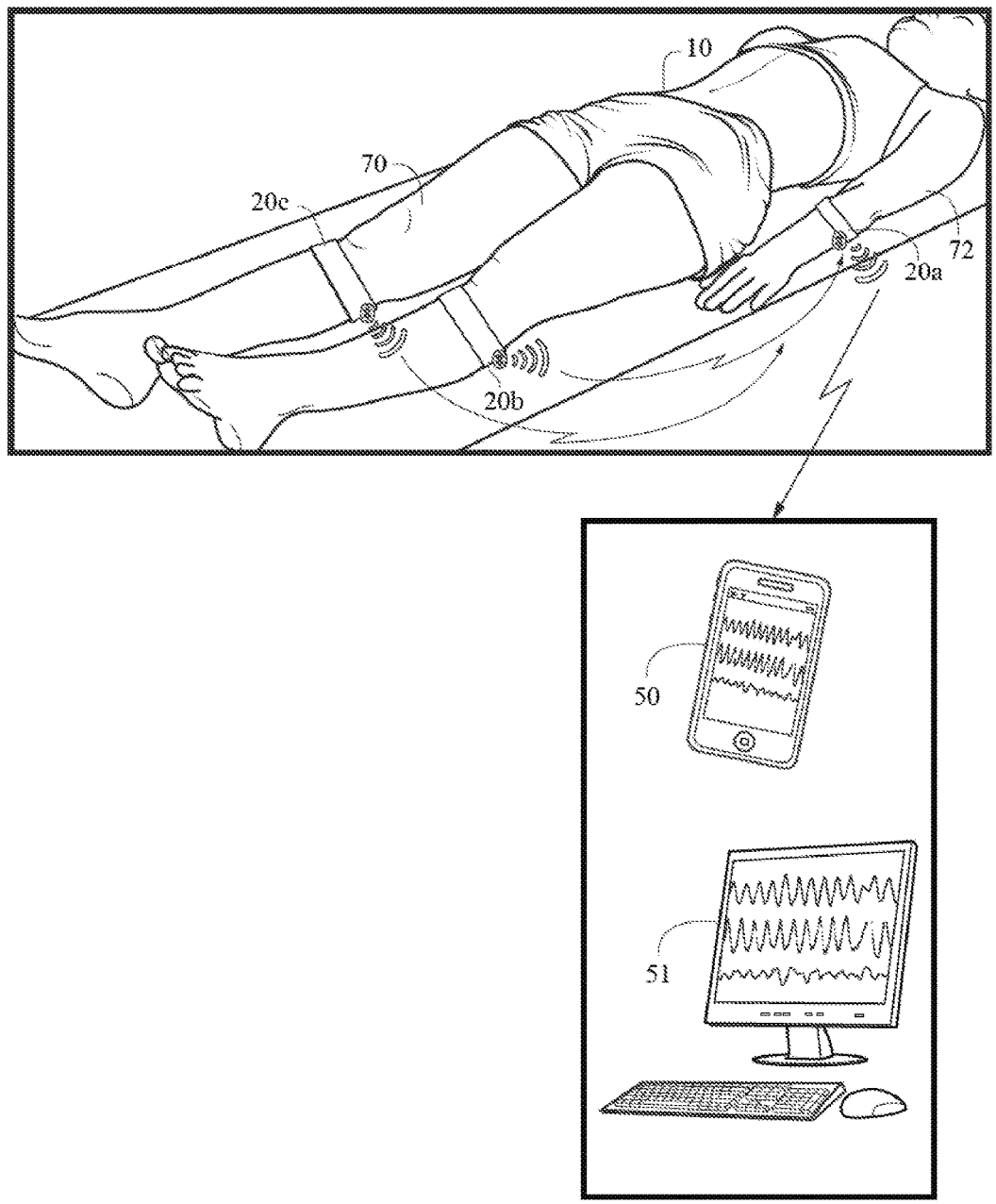
FIG. 1 is a plan view of a preferred embodiment of the present invention.
Figure 2:
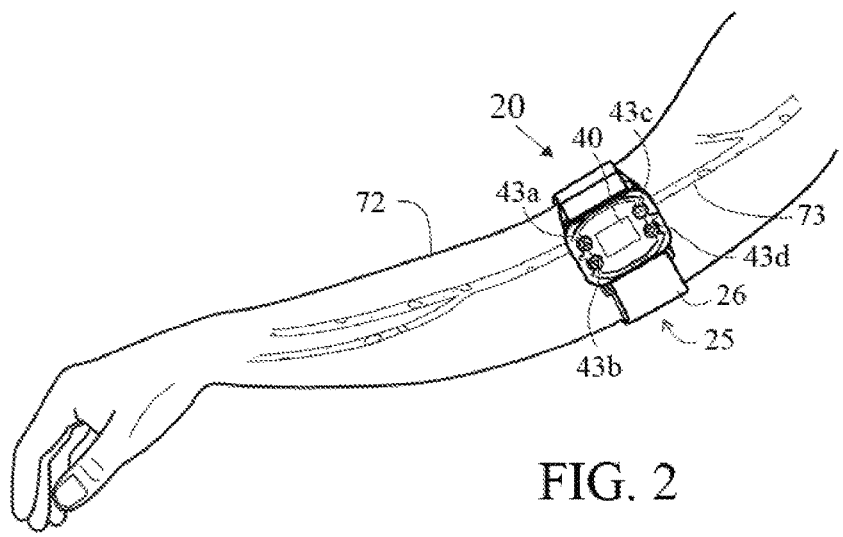
FIG. 2 is a plan view of a monitoring device worn on an arm.
Figure 2A:
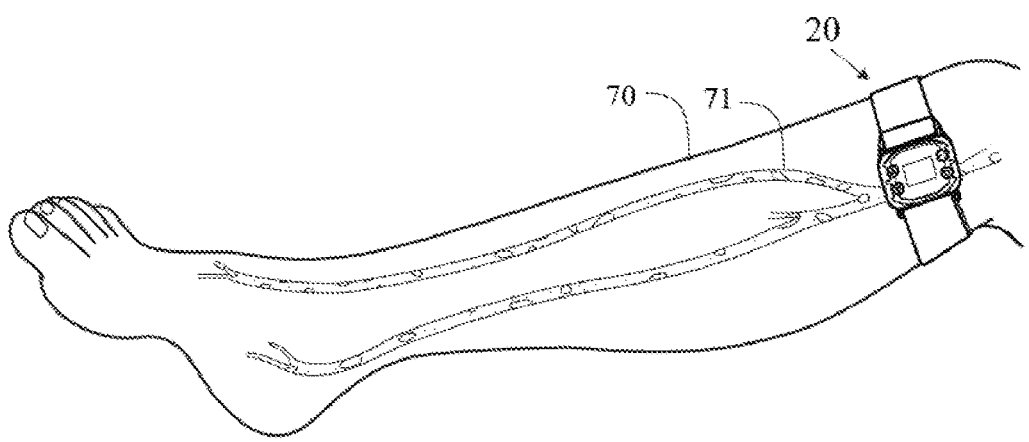
FIG. 2A is a plan view of a monitoring device worn on a leg.
Figure 3:
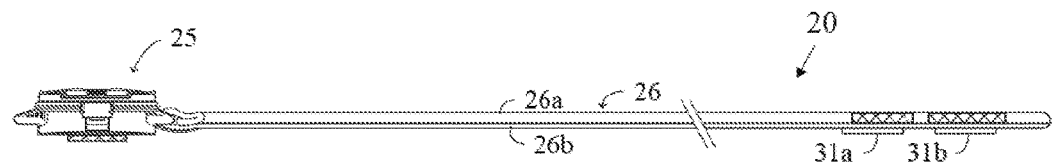
FIG. 3 is a side view of a monitoring device.
Figure 4:
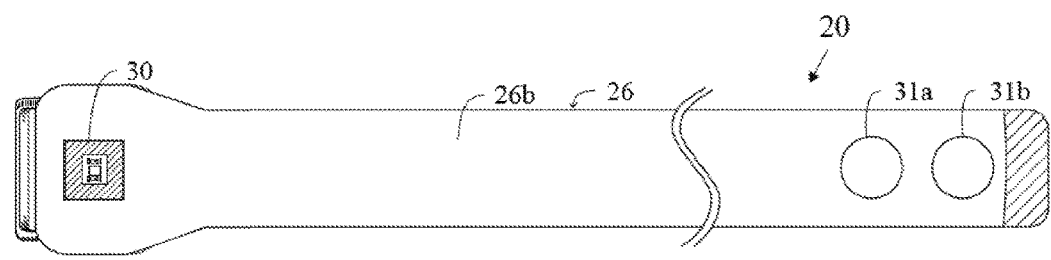
FIG. 4 is an interior surface plan view of a monitoring device.
Figure 5:
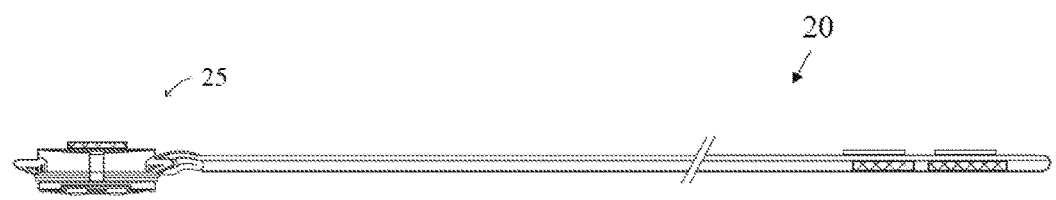
FIG. 5 is a side view of a monitoring device.

FIG. 1 shows a preferred embodiment of the present invention. Monitoring devices 20a-20c are worn on a user 10 in a lying position. A first monitoring device 20a is placed on the left forearm 72. A second monitoring device 20b and a third monitoring device 20c are placed on both legs 70 of the user 10, two inches below the knees. Signals generated from monitoring devices 20b-20c are transmitted wirelessly to monitoring device 20a. The monitoring device 20a then transmits data to a processing device, such as a smart phone 50 or a computer 51.

The processing device, such as a smart phone 50 or a computer 51 preferably has BLUETOOTH or wireless radio to communicate with the monitoring device 20a. Examples of smartphones include the IPHONE® smartphone from Apple, Inc., BLACKBERRY® smartphones from Research In Motion, the DROID® smartphone from Motorola Mobility Inc., GALAXY S® smartphones from Samsung Electronics Co., Ltd, and many more.

The processing device 50 or 51 also has a processor. The processor determines a PAD event for the user 10 based on a difference between amplitudes of pulse waves and a difference between delays of pulse waves.

A monitoring device, as shown in FIGS. 2-6, is generally designated 20. The monitoring device 20 preferably includes an article 25 and an attachment band 26 having an exterior surface 26a and interior surface 26b. The monitoring device 20 is preferably secured with VELCRO® hook and loop material 31a and 31b. The article 25 preferably includes an optical sensor 30, control components 43a-43c and optionally a display member 40. The monitoring device 20 is preferably worn on a user's wrist, arm 72 or leg 70.

The article 25 preferably has a USB port for a wired connection to a computer 51, tablet, video monitor or mobile communication device such as smart phone 50.

It is desirous to adapt the monitoring device 20 to the anatomy of the user's arm 72 or even the user's leg 70. The band 26 is preferably composed of neoprene, leather, synthetic leather, LYCRA, another similar material, or a combination thereof. The article 25 is preferably composed of a semi-rigid or rigid plastic with a rubber-like or semi-flex plastic bottom layer for contact with the user's body. The bottom layer of the article 25 may have a curved surface for contact with a user's body. The article 25 preferably has a mass ranging from 5 grams to 50 grams. Preferably, the lower the mass of the article 25, the more comfort to the user. The article 25 preferably has a thickness ranging from 5 mm to 10 mm, and is most preferably 6.5 mm.

Although the monitoring device 20 is described in reference to an article worn on a user's arm, wrist or leg, those skilled in the pertinent art will recognize that the monitoring device 20 may take other forms such as eyewear disclosed in Brady et al, U.S. Pat. No. 7,648,463, for a Monitoring Device, Method And System, which is hereby incorporated by reference in its entirety or a glove such as disclosed in Rulkov et al., U.S. Pat. No. 7,887,492, for a Monitoring Device, Method And System, which is hereby incorporated by reference in its entirety.

Figure 6:
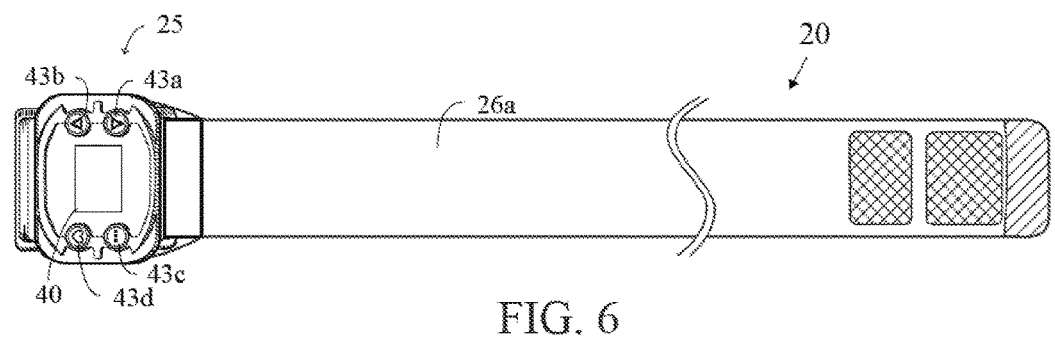
FIG. 6 is an exterior surface view of a monitoring device.
Figure 7:
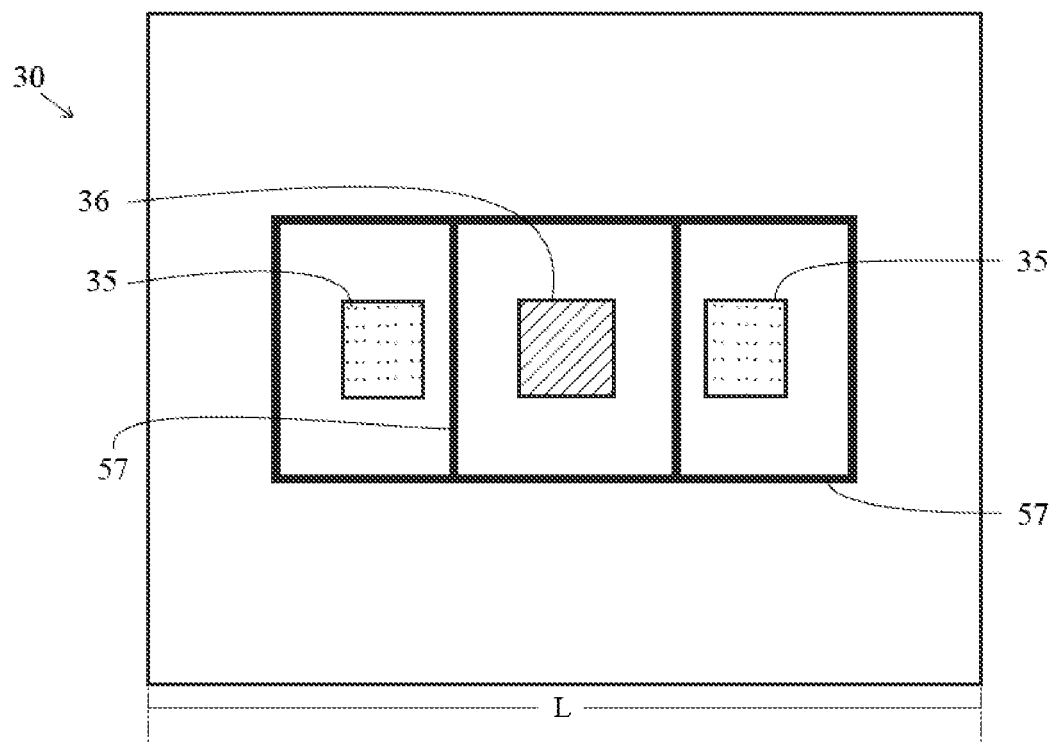
FIG. 7 is an isolated view of the electrical components of a monitoring device.
Figure 8:
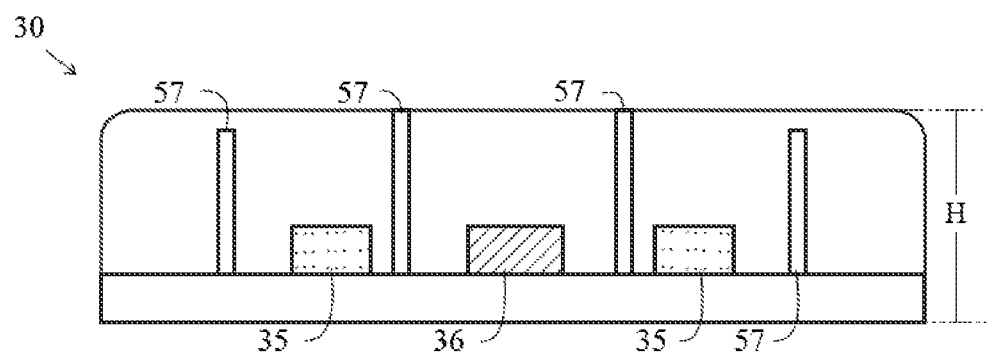
FIG. 8 is isolated side view of the electrical components of a monitoring device.
Figure 9:
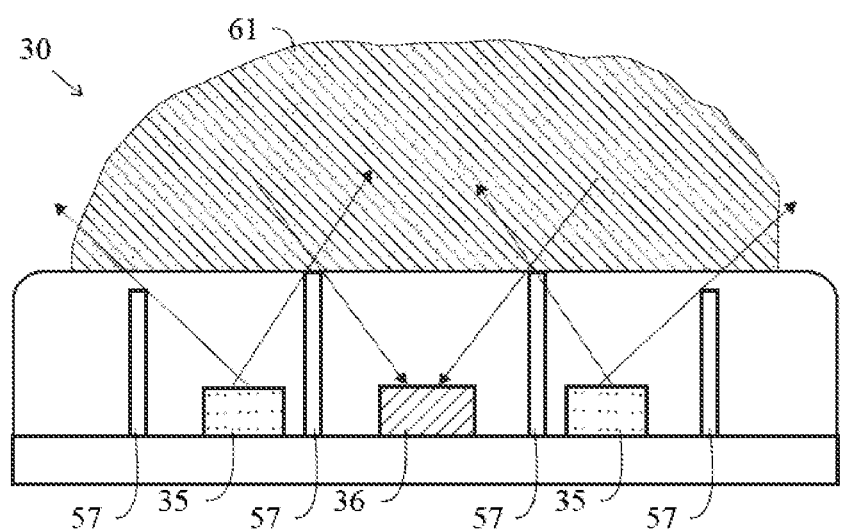
FIG. 9 is an isolated exterior surface view of an optical sensor for a monitoring device.

FIGS. 7-9 illustrate the sensor 30. The sensor 30 has a photodetector 36, at least two LEDs 35 and an opaque light shield 57. The LEDs 35 are preferably green light LEDs of the same wavelength. The sensor 30 preferably has a length, L, of 7-10 mm on each side, as shown in FIG. 6. The sensor 30 preferably has a height, H, of 1-1.5 mm, as shown in FIG. 7. The opaque light shield 57 blocks the direct light from the LEDs 35 to the photodetector 36. Only the green light diffused through the translucent media (skin of the user) 61, as shown in FIG. 8, is allowed to enter the chamber of the photodetector 36. This provides for a more accurate heart rate or vital sign signal. The use of two green LEDs form symmetric light diffusion volume around the sensor. The use of two green LEDs also mitigates mechanical noise.

In a preferred design of the sensor 30, the distance between the centers of active areas of LEDs 35 is preferably 5-6 mm. The active area (photodetector 36) of a sensor 30 is placed in the middle of that distance. In the custom sensor, the distance of a custom sensor is preferably in the range of 3-4 mm (which means the spacing between the centers of photodetector 36 and LEDs 35 is about 1.5-2 mm). The distance is preferably sufficient for the placement of an opaque barrier between them. To control the amplitude of the LED intensity pulse a sufficient current (voltage) range of intensity ramp is used to control the LEDs 35 and to achieve the same levels of intensity in both LEDs 35 within a given range. The electrical characteristics of 520 nm LED in terms of voltage range for intensity ramp is sufficient. The top surface of the sensor 30 is preferably flat and in steady contact with the skin. Under a strong motion condition, the skin moves at the border of the contact surface. The sizes of the sensor area and flat skin contact area are selected to reduce the boundary motion effects. If the distance between the LEDs and sensor is reduced, a lighted area of the skin is smaller, and the contact area is reduced (5×5 mm is acceptable). A non allergenic epoxy is an easy way to seal the contact area from moisture. The preferred embodiment uses a fixed pulse width within the range of 125 to 250 microseconds (μsec) turning on LEDs periodically with period two msec and a TSL13T photodetector 36. The output signal of the sensor 30 is monitored to ensure that it is not saturated. The use of short-term LED pulses combined with a high pass filter to reduce ambient light effects. In the preferred embodiment, voltage is collected at the sensor output every two msec synchronously with the LED pulse. The microprocessor, averages eight consecutive samples in order to improve the SNR (signal to noise ratio) and then works with the averaged numbers. Therefore the sampling rate for raw data is preferably two msec, however if eight-sample averaging is utilized in the integrated sensor the data output rate is reduced to sending a new averaged value every sixteen msec. An ADC with at least 12-bit resolution is used. The response of TSL13T photodiode (from AMS-TAOS USA INC., of Plano Tex.) is acceptable. The detailed description of the sensor and front-end design along with signal processing method is disclosed in U.S. Pat. No. 8,460,199B2, which is hereby incorporated by reference in its entirety.

The optical sensor 30 of the monitoring device 20 is preferably worn on the user's arm 72, wrist, or leg 70. However, those skilled in the pertinent art will recognize that the plethysmographic optical sensor may be placed elsewhere on the body of the user without departing from the scope and spirit of the present invention. In a preferred embodiment, the optical sensor 30 is a plurality of light emitting diodes ("LED") 35, as shown in FIGS. 7-9, based on green light (wavelength of 500-570 nm), wherein the LEDs 35 generate green light, preferably at wavelength of 520 nm, and a photodetector 36 detects the green light. Yet in an alternative embodiment, the optical sensor 30 is a photodetector 36 and a single LED 35 transmitting light at a wavelength of approximately 900 nanometers as a pulsed infrared LED. As the heart pumps blood through the arteries 71 and 73 in the user's arm, wrist, or leg, the photodetector 36, which is typically a photodiode, detects reflectance/transmission at the wavelengths (green, red or infrared), and in response generates a radiation-induced signal.

A preferred optical sensor 30 utilizing green light is a TSL13T light to voltage converter sensor from AMS-TAOS USA INC., of Plano Tex. Output voltage is linear with light intensity (irradiance) incident.

Figure 10:
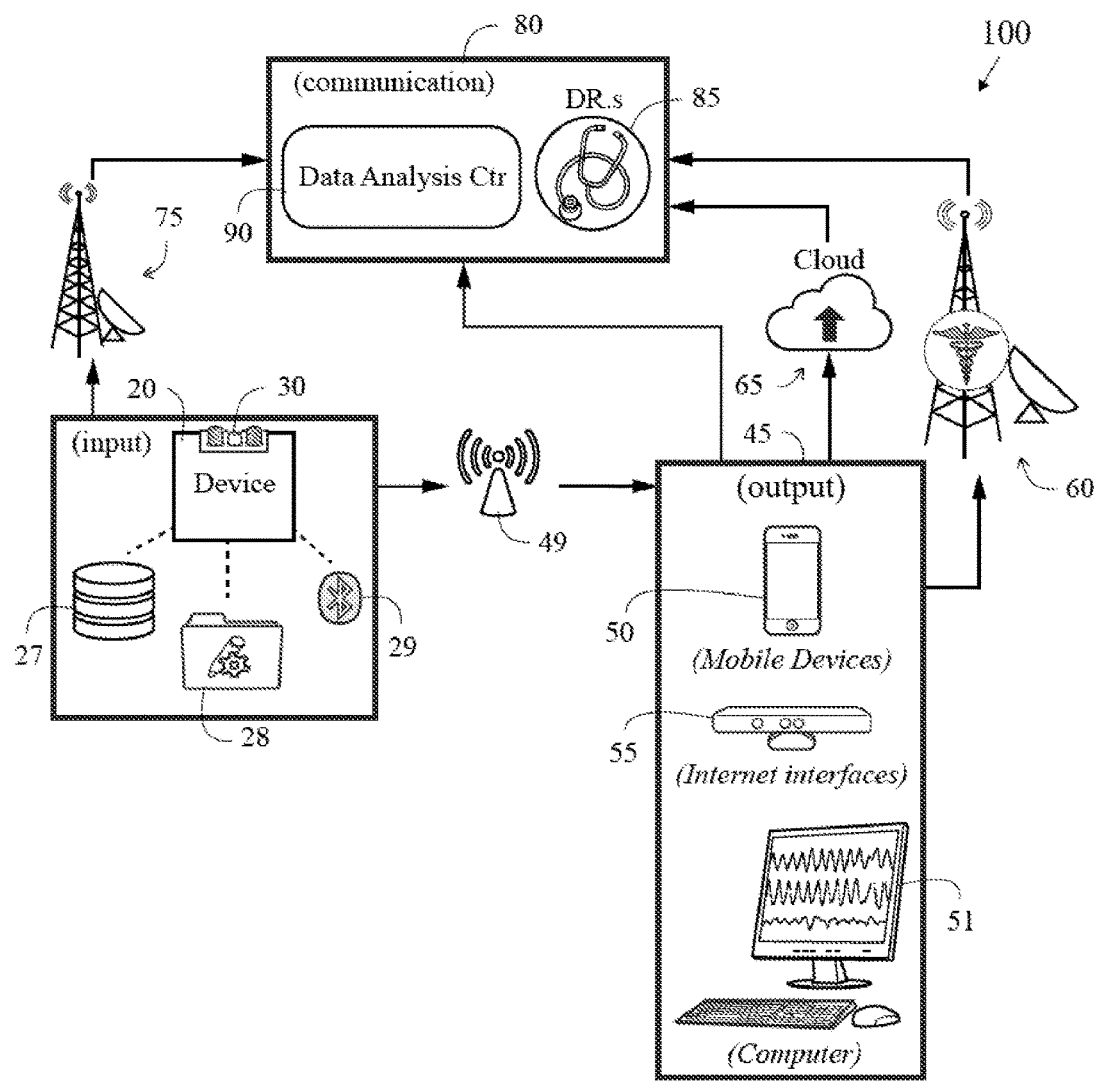
FIG. 10 is a block diagram of a system of the present invention.

In one embodiment, the display member 40 of the monitoring device 20 is removed and the signal is sent to an output device 45 such as a personal digital assistant, computer 51, mobile telephone 50, exercise equipment, gaming device 55, or the like for display and even processing of the user's real-time vital signs information, as shown in FIGS. 1 and 10. Alternatively, the circuitry assembly includes a flexible microprocessor board which is a low power, micro-size easily integrated board which provides blood oxygenation level, pulse rate (heart rate), signal strength bar graph, plethysmogram and status bits data. The microprocessor can also store data. The microprocessor processes the data to display pulse rate, blood oxygenation levels, calories expended by the user of a pre-set time period, target zone activity and time. The display member 40, as shown in FIG. 6, is preferably an Organic Light Emitting Diode (OLED) array. Alternatively, the display member 40 is a liquid crystal display ("LCD") or other similar display device or a Light Emitting Diode (LED).

A microprocessor processes the signal generated from the optical sensor 30 to generate the plurality of vital sign information for the user, which is displayed on the display member 40. The control components 43a-c are connected to the processor to control the input of information and the output of information displayed on the display member 40.

The monitoring device 20 is preferably powered by a power source positioned on the article 25. Preferably the power source is a battery. The power source is preferably a lithium ion rechargeable battery such as available from NEC-Tokin. The power source preferably has an accessible port for recharging. The circuit assembly of the monitoring device preferably operates in a range of 3.5-5 volts and draws a current of 20- to 40 milliamps. An alternative power source is an AA or AAA disposable or rechargeable battery. The power source preferably provides at least 900 milliamp hours of power to the monitoring device 20.

The monitoring device 20 alternatively has a short-range wireless transceiver 29, which is preferably a transmitter operating on a wireless protocol, e.g. BLUETOOTH, part-15, or 802.11. "Part-15" refers to a conventional low-power, short-range wireless protocol, such as that used in cordless telephones. Other communication protocols include a part 15 low power short-range radio, standard BLUETOOTH or BLUETOOTH Low Energy (to conserve power) or other low power short range communications means. The short-range wireless transmitter 29 (e.g., a BLUETOOTH transmitter) receives information from the microprocessor and transmits this information in the form of a packet through an antenna. An external laptop computer or hand-held device features a similar antenna coupled to a matched wireless, short-range receiver that receives the packet. In certain embodiments, the hand-held device is a cellular telephone 50 with a Bluetooth circuit integrated directly into a chipset used in the cellular telephone. In this case, the cellular telephone may include a software application that receives, processes, and displays the information. The secondary wireless component may also include a long-range wireless transmitter that transmits information over a terrestrial, satellite 75, or 802.11-based wireless network 49. Suitable networks include those operating at least one of the following protocols: CDMA, GSM, GPRS, Mobitex, DataTac, iDEN, and analogs and derivatives thereof. Alternatively, the handheld device is a pager or PDA.

A general method is as follows. The light source 35 transmits light through the skin of the user. The photo-detector 36 detects the light. The pulse rate is determined by the signals received by the photo-detector 36.

This information is sent to the microprocessor for creation of user's real-time pulse rate. The microprocessor further processes the information to display pulse rate, calories expended by the user of a pre-set time period, target zones of activity and time. The information is displayed on a display member or electro-optical display.

FIG. 10 shows a system 100 of the present invention. The monitoring device 20 comprises of an optical sensor 30, BLUETOOTH 29 or wireless radio, an application 28, and memory or a database 27. Using BLUETOOTH or a wireless network 49, the monitoring device 20 can send data to output devices 45 such as a mobile smart phone 50, a gaming device 55, or a computer 51. The data can then be sent to a secondary communication node 80, such as to a data analysis center 90 or to a doctor's office 85, via a private cloud 65 or through a dedicated medical communication network 60. If the monitoring device 20 is equipped with a transceiver then data can be sent directly through a cellular network 75 to a secondary communication node 80.

Figure 11:
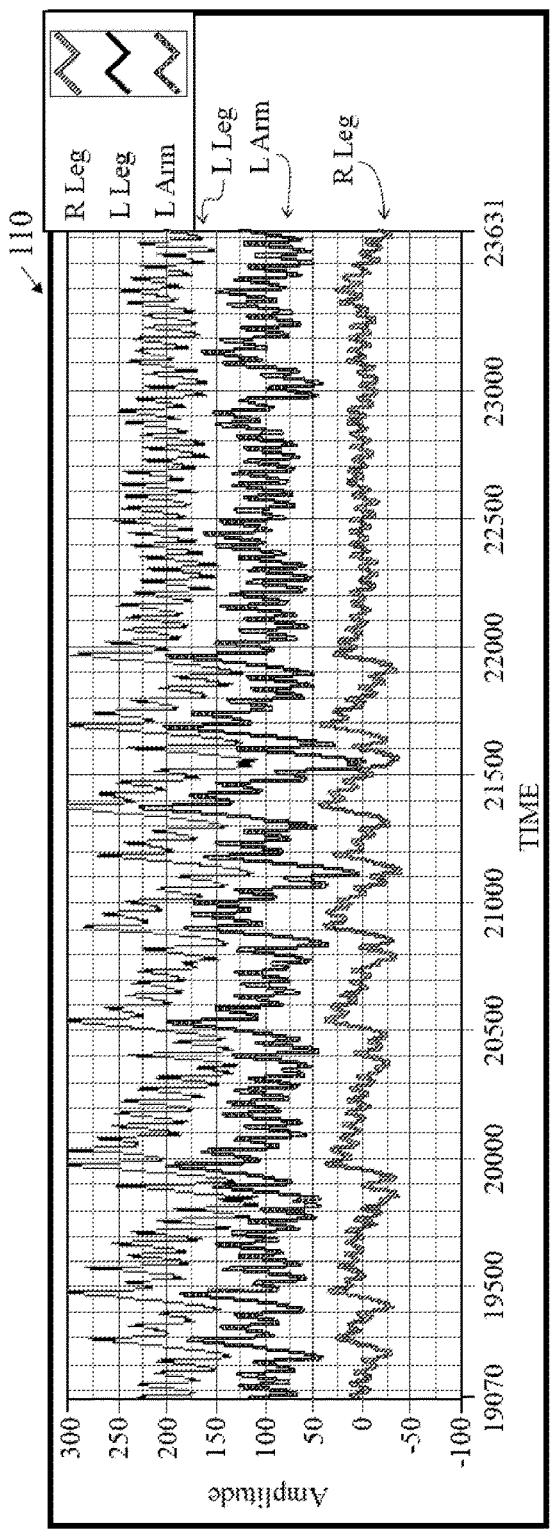
FIG. 11 is a graph of time versus amplitude for signals from three mobile plethysmographic devices attached to user's arm and legs.

FIG. 11 illustrates a graph 110 of amplitude over time of PPG pulses in Right Leg, Left Leg, and Left arm.

Figure 11A:
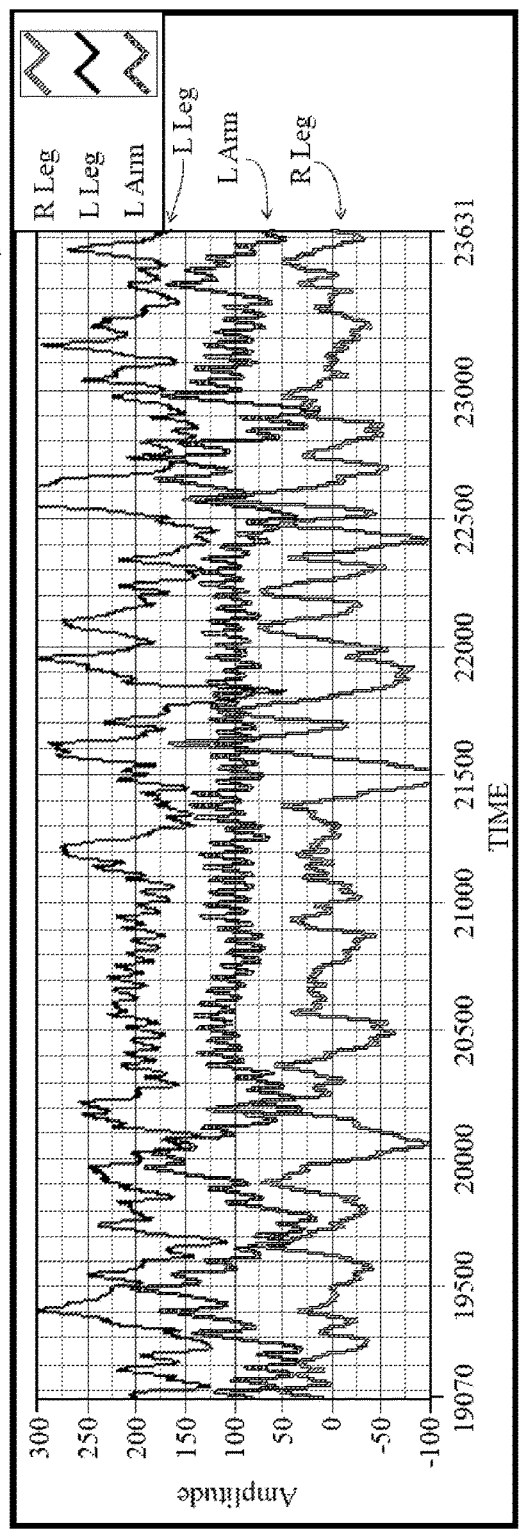
FIG. 11A is a graph of time versus amplitude for signals from three mobile plethysmographic devices attached to user's arm and legs.

FIG. 11A illustrates a graph 110 of amplitude over time of PPG pulses in Right Leg, Left Leg, and Left arm.

Test one had the units turned on in the order of 1) left arm 2) left leg and 3) right leg. The recording was stopped while transitioning from laying to sitting as a wire was unplugged so the second file resumes with the sitting and standing portions of the test.

Test two had the units turned on in the order of 1) left arm 2) right leg below the knee and 3) right leg above the knee.

Figure 12:
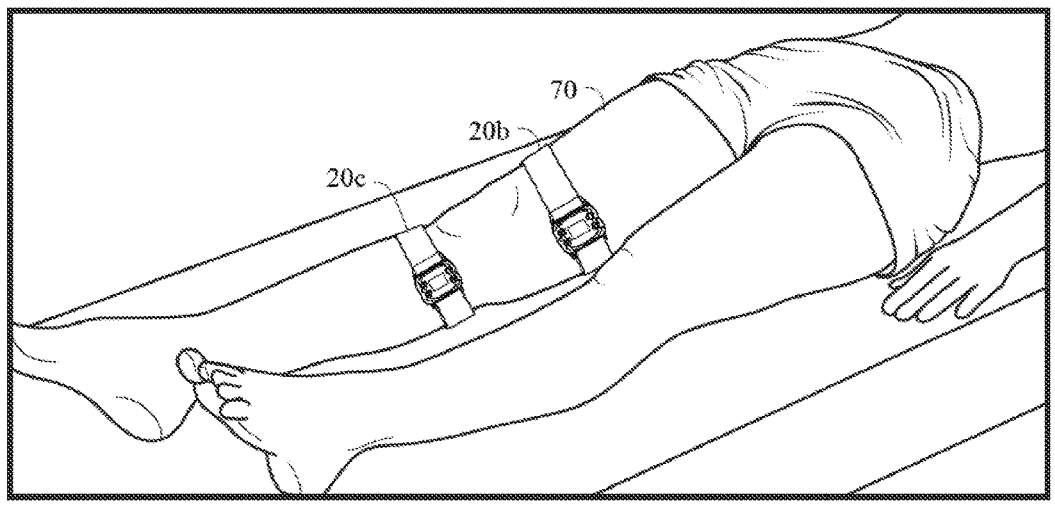
FIG. 12 is a plan view of an embodiment of the placement of the monitoring device.
Figure 13:
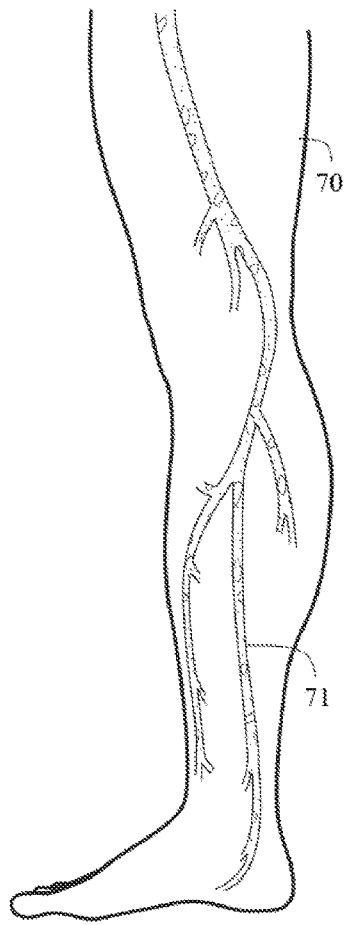
FIG. 13 is a plan view of arteries of the leg.

FIG. 12 shows an alternative placement of monitoring devices 20b-20c on a user's leg 70, using two monitoring devices 20b-20c on the same leg 70. FIG. 13 shows the arteries 71 of a leg 70. The monitoring device 20 measures blood volume and provides a quantitative measure of blood flow in the extremities based on the differential in amplitude in the pleth signal.

Figure 14:
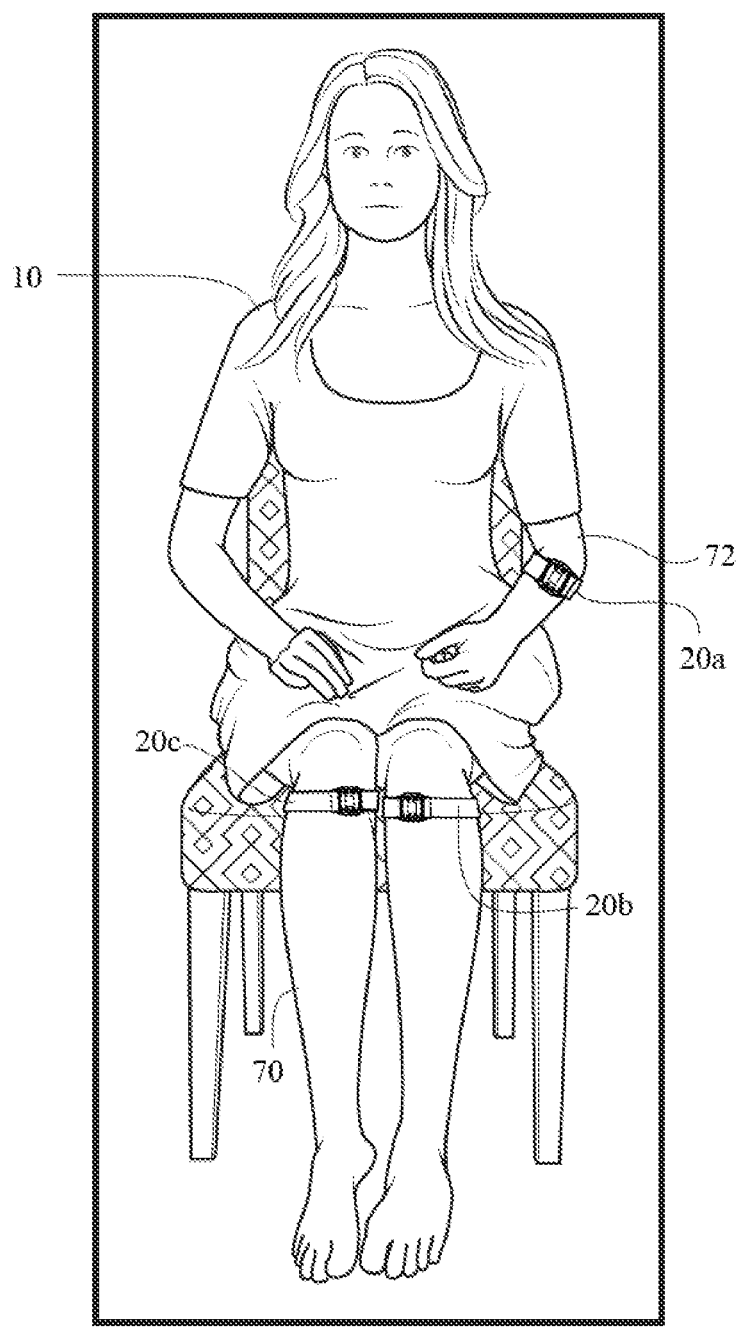
FIG. 14 is a plan view of a preferred embodiment of a monitoring device worn by a user.

FIG. 14 shows another embodiment of a monitoring device worn 20a-20c by a user 10, in a sitting position. Generally, an upper extremity measurement, from the arm 72 is used as to baseline the amplitude measurement from the heart and then compare it to the measurements on each leg 70 from each device 20b-20c thereon.

Figure 19:
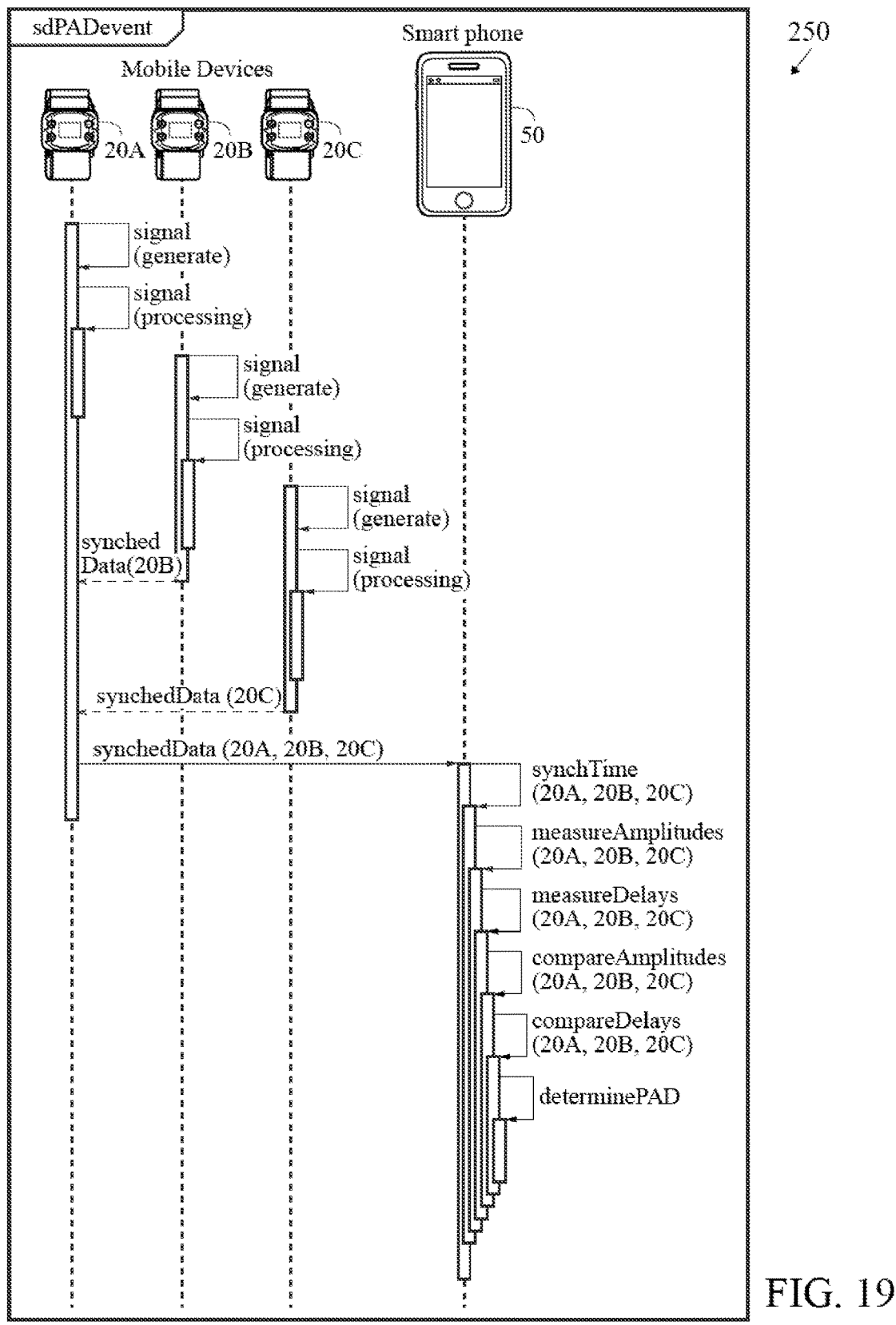
FIG. 19 is a communications sequence diagram for communications between mobile plethysmographic devices and a processing device.

The method for determining a PAD event for a patient begins by generating three signals, as shown in FIGS. 15, 16, 17, and 18. FIG. 19 is a sequence diagram sdPAD event 250 showing the communication between the mobile devices 20a-20c and a processing device, such as a smart phone 50. A first mobile device, monitoring device 20a, with an optical sensor 30 and processor, generates an optical signal and then signal processing includes the optical signal being digitized, processed and synchronized. Generated from the optical signal is a first plethysmographic signal, including a first plurality of pulse waves, for an arm 72 position for a patient 10.

A second mobile device, monitoring device 20b, with an optical sensor 30 and processor, generates an optical signal and then signal processing includes the optical signal being digitized, processed and synchronized. Generated from the optical signal is a second plethysmographic signal, including a second plurality of pulse waves, for an arm 72 position for a patient 10.

A second mobile device, monitoring device 20b, with an optical sensor 30 and processor, generates an optical signal and then signal processing includes the optical signal being digitized, processed and synchronized. Generated from the optical signal is a second plethysmographic signal, including a second plurality of pulse waves, for a right leg 70 position for a patient 10.

A third mobile device, monitoring device 20c, with an optical sensor 30 and processor, generates an optical signal and then signal processing includes the optical signal being digitized, processed and synchronized. Generated from the optical signal is a third plethysmographic signal, including a third plurality of pulse waves, for a left leg 70 position for a patient 10. Each mobile device 20a-20c includes a wireless transceiver for transmitting and receiving wireless communications using a communication protocol.

The synchronized data for the second and third plethysmographic signals is transmitted to the wireless transceiver of the first mobile device 20a.

Then, the synchronized data from each plethysmographic signal, including the synchronized data from the first plethysmographic signal, is transmitted from the wireless transceiver of the first mobile device 20a to a wireless transceiver of a processing device, preferably a smart phone 50 or other smart device, or computer 51. The first, second, and third plethysmographic signals are also time synchronized for comparison on a time basis.

A plurality of amplitudes is measured for each of the pulse waves for the first, second, and third plethysmographic signals.

A plurality of delays is measured for each of the pulse waves for the first, second, and third plethysmographic signals.

A plurality of amplitudes is compared for each of the pulse waves for the first, second, and third plethysmographic signals.

A plurality of delays is compared for each of the pulse waves for the first, second, and third plethysmographic signals.

A PAD event is determined at the processor for the patient 10 based on a difference between the plurality of amplitudes of each of the first, second, and third plurality of pulse waves, and a difference between the plurality of delays of each of the first, second, and third plurality of pulse waves.

FIGS. 15-18A are graphs showing PPG pulses. The presence of PAD can be detected by measuring and comparing amplitudes and delays in PPG pulses in the legs.

The device measures blood volume is an alternative to the above methods and provides a quantitative measure of blood flow in the extremities based on the differential in amplitude in our pleth signal between the arm and the two lower extremities. The changes in amplitude from the arm and one or both lower extremities can indicate PAD. When measurements are taken over time they can also be used to diagnose the progression of the disease and support effective treatment.

FIGS. 15-18 illustrate PAD data. There are some signatures of PAD in Patient 1 data. In Patient 2 they are not clear. The presence of PAD could be detected by measuring and comparing amplitudes and delays in PPG pulses in the legs.

Figure 15:
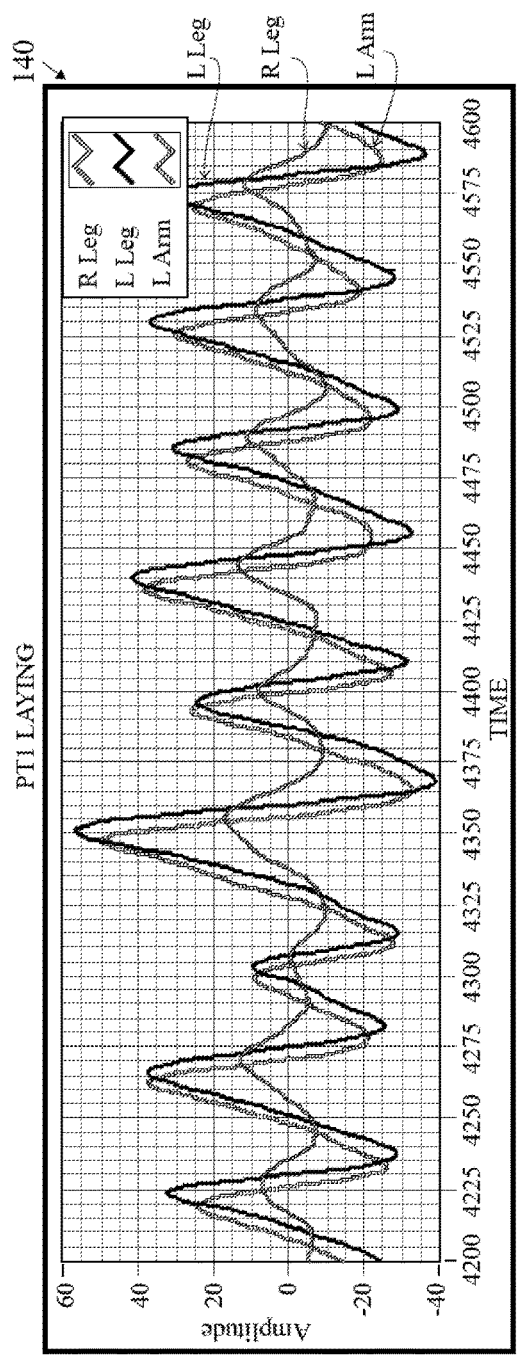
FIG. 15 is a graph of time versus amplitude for a $1^{st}$ patient lying down.
Figure 15A:
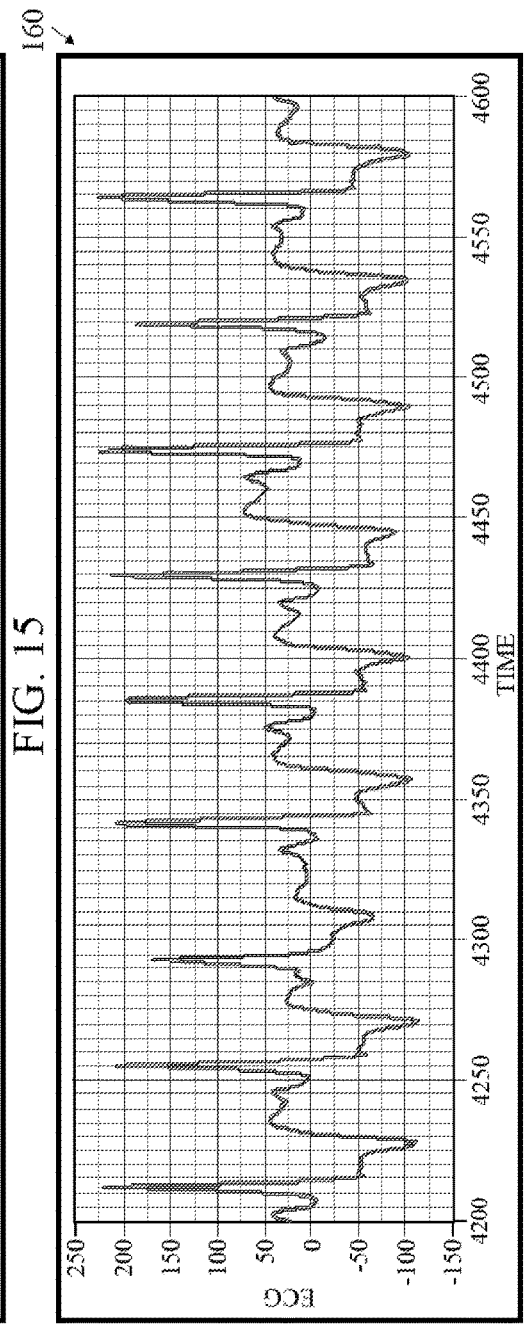
FIG. 15A is a graph of time versus amplitude for an ECG.

FIG. 15 shows that the amplitude of PPG pulses in a user's right leg is significantly less than in the user's left leg. The pulse propagation delays in the legs are different.

Figure 16:
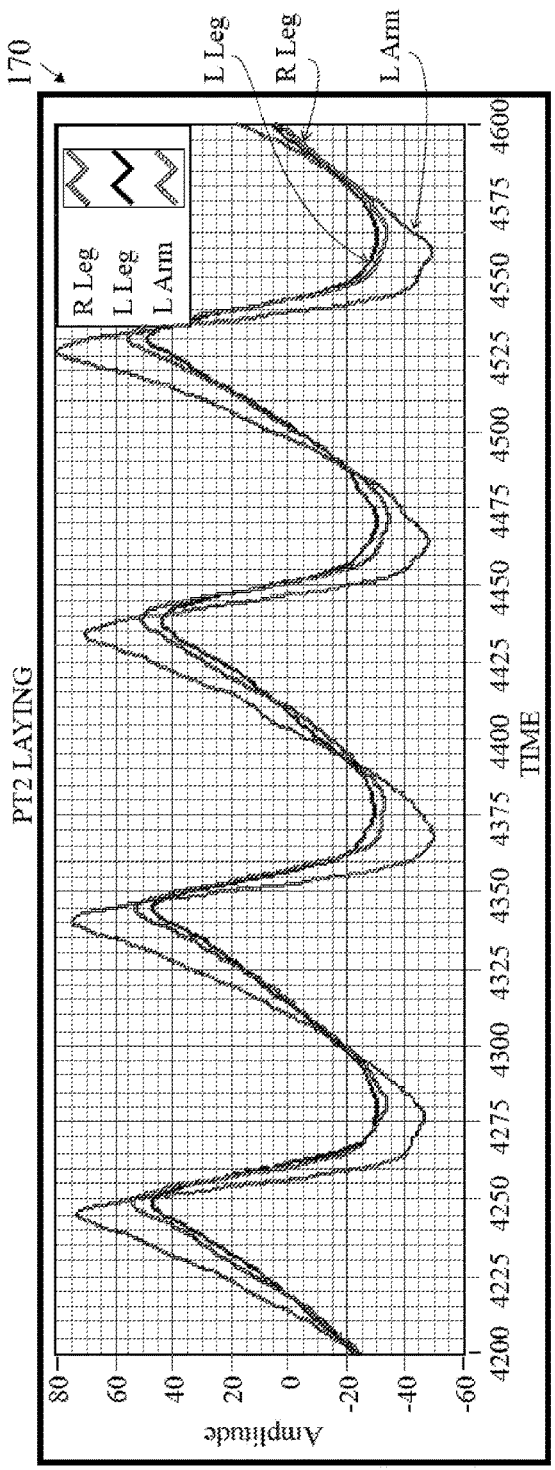
FIG. 16 is a graph of time versus amplitude for a $2^{nd}$ patient lying down
Figure 16A:
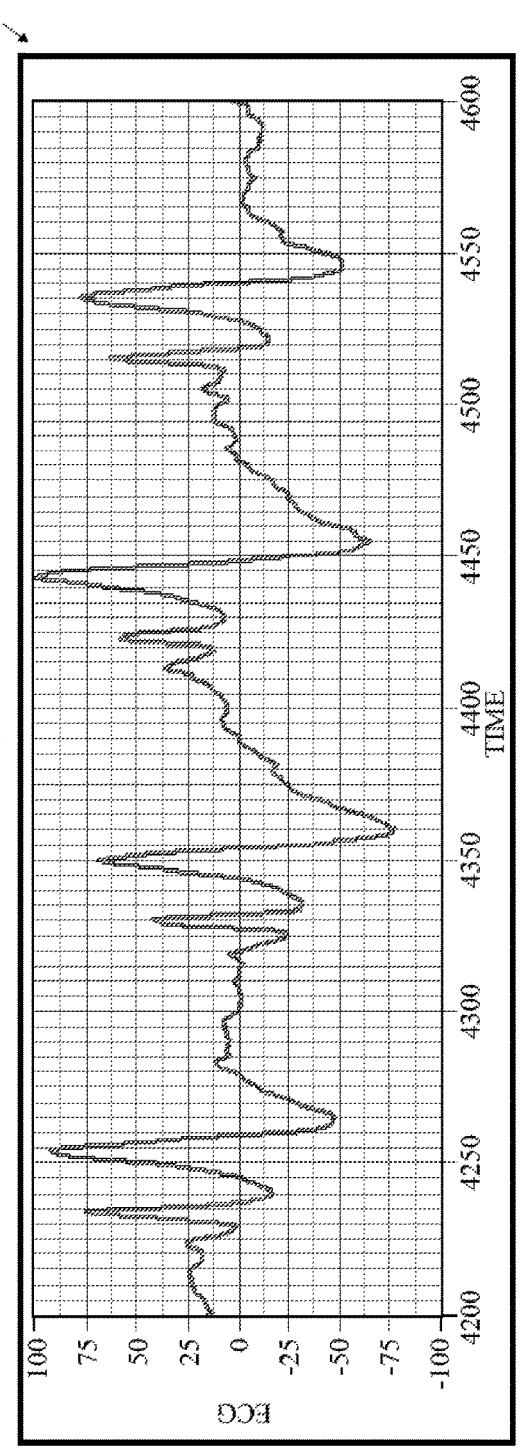
FIG. 16A is a graph of time versus amplitude for an ECG.

FIG. 16 shows that the amplitude of PPG pulses in a user's right and left legs are similar. The pulse propagation delays in the legs are about the same.

Figure 17:
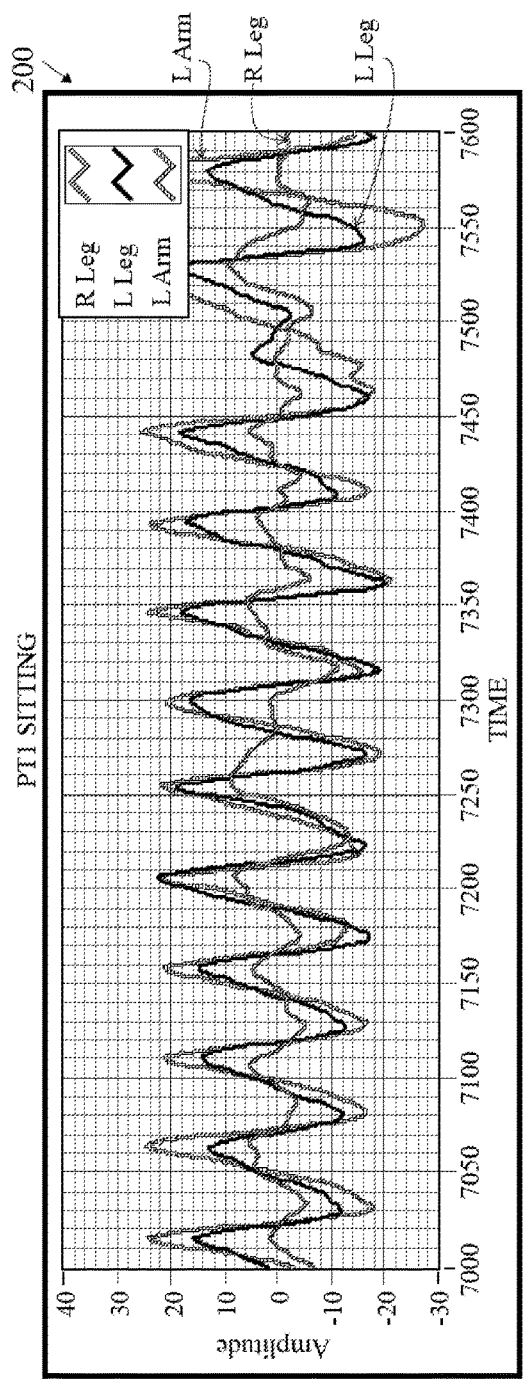
FIG. 17 is a graph of time versus amplitude for a $1^{st}$ patient sitting up.
Figure 17A:
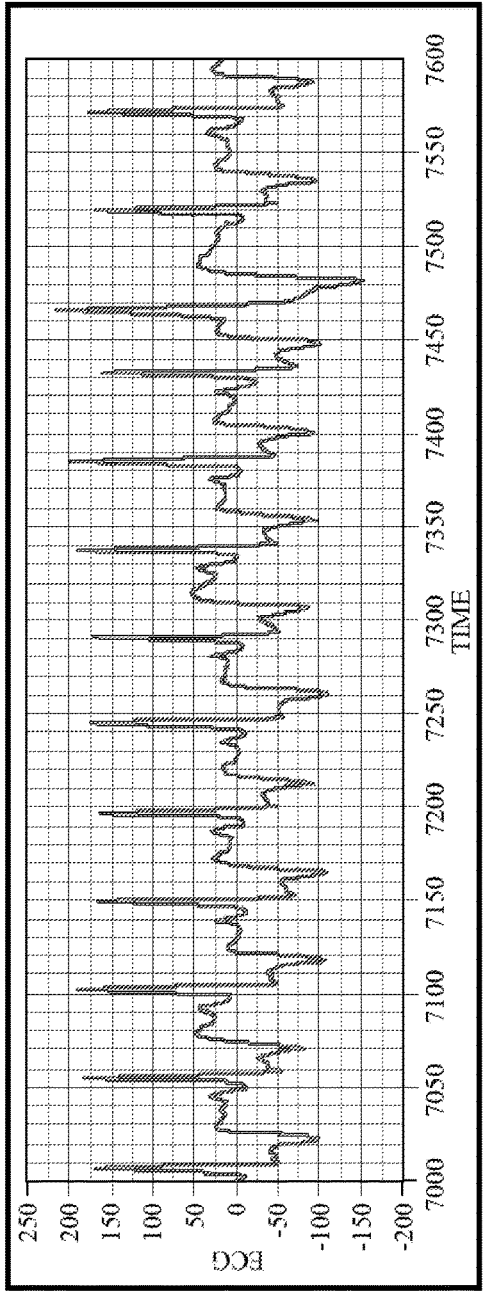
FIG. 17A is a graph of time versus amplitude for an ECG.

FIG. 17 shows that the amplitude of PPG pulses in a user's right leg is significantly less than in the user's left leg. The pulse propagation delays in the legs are about the same. Shapes of the pulses are different FIG. 18 shows that the amplitude of PPG pulses in a user's right and left legs are different. The pulse propagation delays in the legs are about the same.

When light is applied to a body part, such as the arm 72, a PPG waveform, as shown in FIG. 11, is obtained through reflection of the applied light, the LEDs 35 of the monitoring device 20. Photoplethysmographic signals given by the intensity of the LED light received by the photo sensor after it is attenuated in the skin. Total attenuation of the light is composed of a pulsatile component (ac) and non-pulsatile component (dc). AC is a change in blood flow, which reflects a change in a blood stream due to heartbeat and related to arterial pulsation, while DC is related to light absorption in the tissue, vein, and diastolic arterial blood volume. The PPG Waveform is obtained by measuring intensity of light after it has been attenuated in the skin. This intensity has an AC compliment that is inverse to the ac attenuation that occurred due to the heartbeat.

The system and method described herein may be used with the monitoring device comprising an accelerometer disclosed in Rulkov et al., U.S. Pat. No. 8,579,827 for a Monitoring Device With An Accelerometer, Method And System, which is hereby incorporated by reference in its entirety.

FIG. 20 illustrates a graph 105 of a PPG 110 and ECG 115. A portion of the PPG 110 is further shown in FIG. 22. The PPG is generated by the mobile plethysmographic device 20.

FIG. 20A illustrates a graph 120 of motion detected by an X 121, Y 122, and Z 123 accelerometer. A motion sensor is included to assist in identifying motion noise and filtering the noise from the signal sent by the sensor 30. The motion sensor, such as an accelerometer, is integrated into the circuitry and software of the mobile plethysmographic device 20. As the motion sensor detects an arm swinging, the noise component is utilized with the signal processing noise filtering techniques to provide additional filtering to remove the noise element and improve the accuracy of the mobile plethysmographic device 20. More specifically, the signal from the optical sensor 30 is transmitted to a custom adaptive filter before being sent to a heart beat tracking system and then transmitted to a heart rate beat output. The heart rate beat output provides feedback to the custom adaptive filter, which also receives input from the motion sensor.

In one embodiment, a first systolic pulse peak and a second systolic pulse peak has a first time interval. The amplitude of the first waveform is a measurement from a first valley to the first peak. The amplitude of the second waveform is the measurement from the first valley to the first peak.

Figure 22:
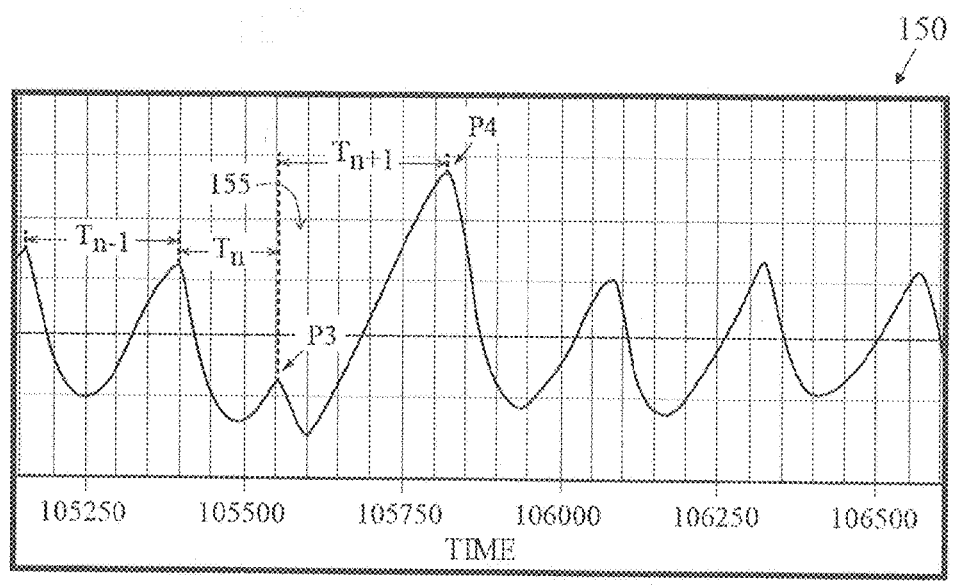
FIG. 22 is a detailed graph of time versus amplitude from FIG. 10 for an example PAC event of a PPG waveform.

FIG. 22 illustrates a graph 150 of an example PAC event as a PPG waveform. As illustrated, a PAC event 155 occurs when time interval between peak P3 and previous peak is shorter than previous time interval and followed by a longer time interval, measured between peaks P3 and P4.

Figure 23:
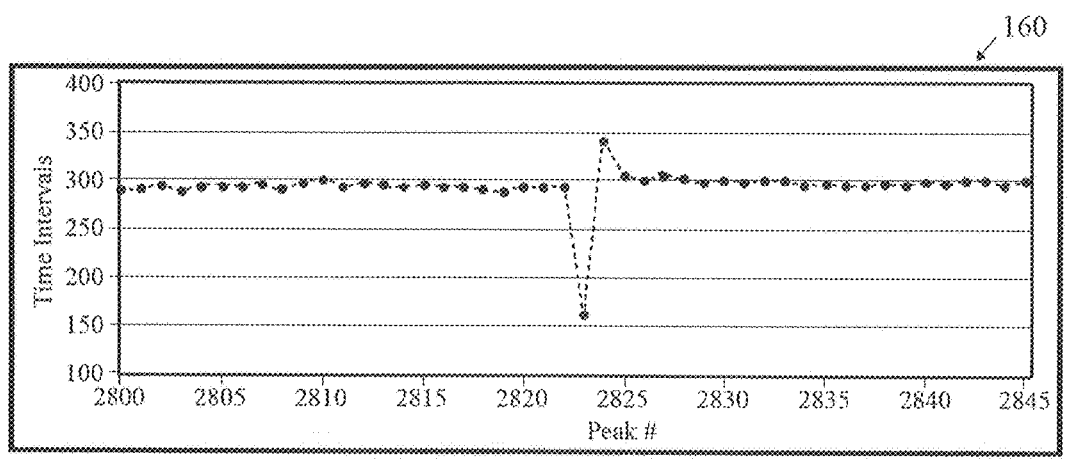
FIG. 23 is a plot graph of time versus amplitude for an example PAC event.
Figure 23A:
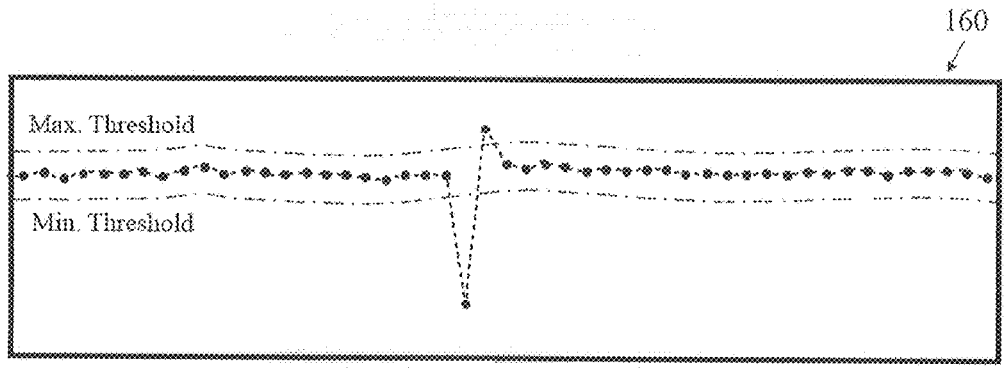
FIG. 23A is a graph illustrating a maximum threshold and a minimum threshold for the peak number.

FIG. 23 illustrates a plot 160 of an example PAC event as it occurs in the sequence of time intervals between the nearby peaks. As illustrated, a PAC event occurs when a short time interval is followed by a longer time interval, both outside the thresholds. FIG. 23A illustrates the maximum threshold and minimum threshold for the time intervals, and illustrates the PAC event, which is a short time interval that occurs outside of the minimum threshold followed immediately by a longer time interval that occurs outside of the maximum threshold.

Figure 21:
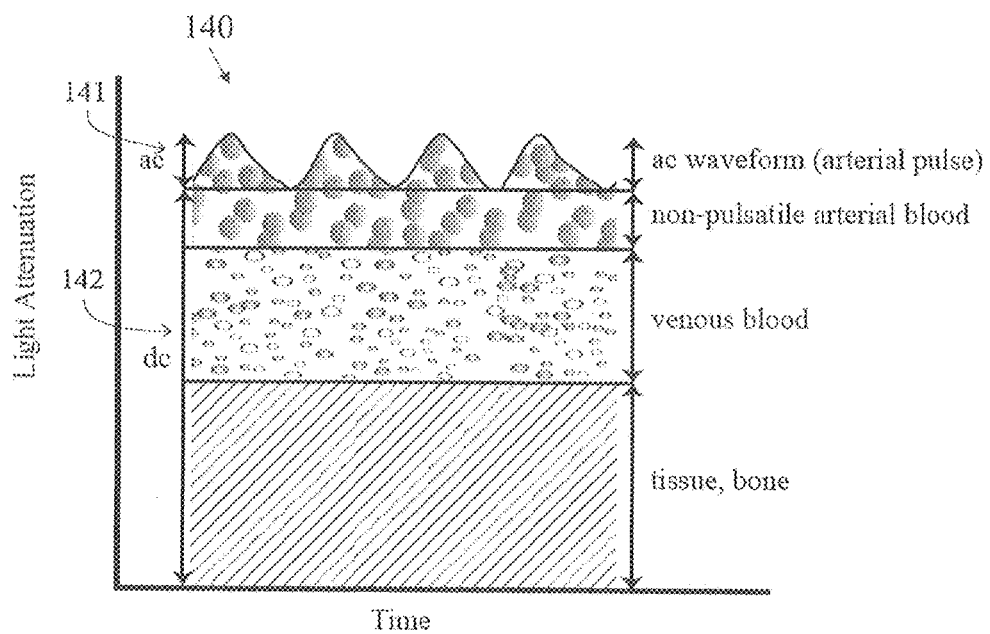
FIG. 21 is a graph of time versus light intensity for a waveform.

When light is applied to a body part, such as the arm 72, a PPG waveform, as shown in FIG. 21, is obtained through reflection of the applied light, the LEDs 35 of the mobile plethysmographic device 20. Photoplethysmographic signals given by the intensity of the LED light received by the photo sensor after it is attenuated in the skin. Total attenuation of the light is composed of a pulsatile component (ac) 141 and nonpulsatile component (dc) 142, as shown in FIG. 11. AC 141 is a change in blood flow, which reflects a change in a blood stream due to heartbeat and related to arterial pulsation, while DC is related to light absorption in the tissue, vein, and diastolic arterial blood volume. The PPG Waveform is obtained by measuring intensity of light after it has been attenuated in the skin. This intensity has an AC compliment that is inverse to the ac attenuation that occurred due to the heartbeat.

The method for determining a premature atrial contraction event for a patient using the mobile plethysmographic device 20 begins with generating a plethysmographic signal. The plethysmographic signal 110, as shown in FIG. 20, for a patient is generated from an optical signal generated by an optical sensor 30 and digitized and processed by a processor, which is then measured. The optical sensor 30 and the processor are on the mobile plethysmographic device 20. The plethysmographic signal 110 comprises multiple pulse waves. A maximum peak value for each pulse wave of the multiple pulse waves of the plethysmographic signal is identified at the processor to generate maximum values of the plethysmographic signal. Time intervals between adjacent maximum values of the plethysmographic signal are calculated at the processor. As shown in FIG. 23A, a threshold minimum time interval and a threshold maximum time interval for the time intervals are established at the processor. As shown in FIG. 22, a premature atrial contraction event for the patient is determined at the processor based on an identification of a time interval that is below the threshold minimum time interval followed immediately by a time interval that is above the threshold maximum time interval.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. A system for determining a premature atrial contraction event for a patient, the system comprising:
 a mobile plethysmographic device adapted to be worn on a patient, the mobile plethysmographic device comprising a processor, a memory, an optical sensor and an accelerometer, wherein the optical sensor comprises a plurality of green LEDs and a photodetector, each of the plurality of the green LEDs having a wavelength ranging from 500 nanometers to 570 nanometers; and
 a display;
 wherein the optical sensor is configured to generate an optical signal for the patient through reflection of an applied light from the plurality of green LEDs of the optical sensor and the intensity of the reflected light is received by the photodetector;

wherein the processor is configured to generate a plethysmographic signal for the patient from the optical signal, the plethysmographic signal comprising a plurality of pulse waves;

wherein the processor is configured to identify a maximum peak value for each pulse wave of the plurality of pulse waves of the plethysmographic signal to generate a plurality of maximum values of the plethysmographic signal;

wherein the processor is configured to calculate a plurality of time intervals between adjacent maximum values of the plethysmographic signal;

wherein the processor is configured to establish a threshold minimum time interval and a threshold maximum time interval for the plurality of time intervals; and wherein the processor is configured to determine a premature atrial contraction event for the patient based on an identification of a time interval that is below the threshold minimum time interval followed immediately by a time interval that is above the threshold maximum time interval;

wherein the processor is configured to monitor for movement of the mobile plethysmographic device using the accelerometer to provide a signal for the movement of the mobile plethysmographic device;

wherein the processor is configured to use accelerometer information from the accelerometer to validate the premature atrial contraction event by measuring motion activity and verifying the validity of the premature atrial contraction event when the motion measured by the accelerometer remains less than a preset threshold.

2. The system according to claim 1 wherein the processor is configured to record the premature atrial contraction event as a first premature atrial contraction event in the memory of the mobile plethysmographic device.

3. The system according to claim 1 wherein the processor is configured to transmit the premature atrial contraction event information from the mobile plethysmographic device to a processing device using a transceiver on the mobile plethysmographic device.

4. The system according to claim 1 wherein the processor is configured to use three axis accelerometer information from the accelerometer to validate the premature atrial contraction event by measuring motion activity and verifying the validity of the premature atrial contraction event when the motion measured by the accelerometer remains less than a preset threshold.

5. A mobile plethysmographic device for determining an arrhythmia event for a patient, the mobile plethysmographic device comprising:

a processor;

a memory;

an optical sensor comprising a plurality of green LEDs and a photodetector, each of the plurality of the green LEDs having a wavelength ranging from 500 nanometers to 570 nanometers; and an accelerometer;

wherein the mobile plethysmographic device is adapted to be worn on a patient;

wherein the optical sensor is configured to generate an optical signal for the patient through reflection of an applied light from the plurality of green LEDs of the optical sensor and the intensity of the reflected light is received by the photodetector;

wherein the processor is configured to generate a plethysmographic signal for the patient from the optical signal, the plethysmographic signal comprising a plurality of pulse waves;

wherein the processor is configured to identify a maximum peak value for each pulse wave of the plurality of pulse waves of the plethysmographic signal to generate a plurality of maximum values of the plethysmographic signal;

wherein the processor is configured to calculate a plurality of time intervals between adjacent maximum values of the plethysmographic signal;

wherein the processor is configured to establish a threshold minimum time interval and a threshold maximum time interval for the plurality of time intervals; and wherein the processor is configured to determine an arrhythmia event for the patient based on an identification of a time interval that is outside of the threshold minimum time interval or maximum time interval followed immediately by a time interval that is above the threshold maximum time interval or minimum time interval;

wherein the processor is configured to monitor for movement of the mobile plethysmographic device using the three axis accelerometer to provide a signal for the movement of the mobile device;

wherein the processor is configured to use three axis accelerometer information from the accelerometer to validate the arrhythmia event by measuring motion activity and verifying the validity of the arrhythmia event when the motion measured by the accelerometer remains less than a preset threshold.

6. The mobile plethysmographic device according to claim 5 wherein the arrhythmia event is one of tachycardia, bradycardia, peripheral artery disease, premature atrial contractions and premature ventricular contractions.

* * * * *